US011305050B2

(12) United States Patent
Jardret et al.

(10) Patent No.: US 11,305,050 B2
(45) Date of Patent: Apr. 19, 2022

(54) CONNECTOR WITH VALVE FOR NEGATIVE PRESSURE WOUND THERAPY SYSTEM

(71) Applicant: DeRoyal Industries, Inc., Powell, TN (US)

(72) Inventors: Vincent Denis Jardret, Powell, TN (US); Jonathan Matthew Cayce, Knoxville, TN (US); Walter Cleveland Cowart, Blaine, TN (US); Scott Douglas Barnes, Knoxville, TN (US); Gregory S. Hodge, Knoxville, TN (US)

(73) Assignee: DeRoyal Industries, Inc., Powell, TN (US)

( * ) Notice: Subject to any disclaimer, the term of this patent is extended or adjusted under 35 U.S.C. 154(b) by 93 days.

(21) Appl. No.: 16/575,921

(22) Filed: Sep. 19, 2019

(65) Prior Publication Data

US 2020/0086018 A1    Mar. 19, 2020

Related U.S. Application Data

(60) Provisional application No. 62/733,128, filed on Sep. 19, 2018.

(51) Int. Cl.
| | |
|---|---|
| *A61M 1/00* | (2006.01) |
| *A61M 39/22* | (2006.01) |
| *A61F 13/00* | (2006.01) |
| *A61M 39/10* | (2006.01) |
| *A61M 39/28* | (2006.01) |

(52) U.S. Cl.
CPC ......... *A61M 1/86* (2021.05); *A61F 13/00068* (2013.01); *A61M 1/743* (2021.05); *A61M 1/842* (2021.05); *A61M 1/85* (2021.05); *A61M 39/105* (2013.01); *A61M 39/1011* (2013.01); *A61M 39/22* (2013.01); *A61M 39/28* (2013.01); *A61M 2205/3331* (2013.01)

(58) Field of Classification Search
CPC .............. A61M 1/0086; A61M 1/0035; A61M 39/1011; A61M 39/105; A61M 1/0082; A61M 39/22; A61M 2039/082; A61M 39/284; A61M 2039/1077
See application file for complete search history.

(56) References Cited

U.S. PATENT DOCUMENTS

| | | |
|---|---|---|
| 3,626,938 A | 12/1971 | Versaci |
| 6,177,049 B1 | 1/2001 | Schnell et al. |
| D649,240 S | 11/2011 | Lewis et al. |

(Continued)

FOREIGN PATENT DOCUMENTS

WO    WO-2016166346 A1 * 10/2016 .......... A61M 39/223

OTHER PUBLICATIONS

Engineering drawings for applicant prior art system with confidential information redacted.

(Continued)

*Primary Examiner* — Susan S Su
*Assistant Examiner* — Eric Rassavong
(74) *Attorney, Agent, or Firm* — Luedeka Neely Group, PC

(57) ABSTRACT

A negative pressure wound therapy device that includes a first tubing connectable in flow communication with a source of negative pressure configured for application of negative pressure to a wound site, a second tubing in flow communication with the wound site, and a valve.

16 Claims, 6 Drawing Sheets

(56) References Cited

U.S. PATENT DOCUMENTS

| | | | |
|---|---|---|---|
| 8,246,592 B2* | 8/2012 | Lockwood | A61F 13/0216 |
| | | | 604/313 |
| 8,356,629 B2* | 1/2013 | Koyama | A61M 39/223 |
| | | | 137/625.19 |
| 8,556,873 B2* | 10/2013 | Bjerregaard | F16K 27/065 |
| | | | 604/327 |
| 9,408,751 B2 | 8/2016 | Heaton | |
| D783,815 S | 4/2017 | Lewis et al. | |
| D785,790 S | 5/2017 | Lewis et al. | |
| 9,797,528 B2 | 10/2017 | Veneroni et al. | |
| 9,907,888 B2 | 3/2018 | Coulthard et al. | |
| 9,956,328 B2 | 5/2018 | Long | |
| 10,016,541 B2 | 7/2018 | Perkins et al. | |
| 2005/0004534 A1* | 1/2005 | Lockwood | A61M 1/74 |
| | | | 604/304 |
| 2007/0287953 A1 | 12/2007 | Ziv et al. | |
| 2010/0211022 A1 | 8/2010 | Harr et al. | |
| 2017/0067568 A1* | 3/2017 | Duncan | F16K 35/04 |

OTHER PUBLICATIONS

International Search Report and Written Opinion for PCT/US19/51934, dated Dec. 6, 2019, 15 pages.

* cited by examiner

CONNECTOR WITH VALVE FOR NEGATIVE PRESSURE WOUND THERAPY SYSTEM

CROSS-REFERENCE TO RELATED APPLICATION

This application claims priority to U.S. Provisional Application No. 62/733,128 filed Sep. 19, 2018, entitled CONNECTOR WITH VALVE FOR NEGATIVE PRESSURE WOUND THERAPY SYSTEM, incorporated herein by reference in its entirety.

FIELD

This disclosure relates to the field of medical conduits. More particularly, this disclosure relates to flow control devices for medical conduits and, in particular, to connectors having valves and configured for use with tubing of negative pressure lines of the type used in negative pressure wound therapy in which negative air pressure is applied to a wound site of a patient. Connectors of the disclosure are advantageously configured to have a compact size and low profile to reduce the risk for injury and to avoid a change in state of the valve if a patient lies on the connector and valve.

BACKGROUND

In certain medical applications, conduits are used to supply or extract fluids to or from a patient. These conduits sometimes need to be obstructed to enable disconnection or to interrupt a process, such as during Negative Pressure Wound Therapy (NPWT).

Traditionally, in some applications such as NPWT, these conduits are temporarily obstructed by the use of clamps applied to PVC tubing to enable disconnection or interruption. An example of a prior art traditional clamp applied to PVC tubing is shown in FIG. 1. These clamps require substantial force to operate, and it may be unclear to an untrained user whether the clamp has effectively completely obstructed the tubing or not. In addition, the clamp represents a potential cause for a pressure injury or discomfort if the patient happens to lie/rest on top of the clamp, due to its bulky shape around the tubing. In such cases, the tubing could also inadvertently be obstructed if the patient lies on top of the clamp and the body weight of the patient closes the clamp, thereby undesirably interrupting the negative pressure therapy provided to that patient.

What is desired is a flow controller structure for NPWT that has positive closure and that is uncomplicated and easy to use. It is also desired that a flow controller have a low profile and compact size and be configured to reduce the risk for injury to a patient or a change in state of the flow controller if the patient lies down on it.

SUMMARY

The current disclosure relates to flow controller structures provided by connector assemblies that incorporate a valve and are configured for use with tubing lines of negative pressure wound therapy devices. The connector assemblies are configured so that they may be easily actuated by a user without requiring excessive levels of force, and clearly indicate when in an open orientation and when in a closed orientation. The valve as incorporated into the assembly provides positive closure when closed. The connector assemblies also have a low profile and compact size and are configured to reduce the risk for injury to a patient or a change in state of the valve if the patient lies down on it.

In one aspect, a connector assembly according to the disclosure is configured for connecting between a first tubing from a source of negative pressure configured for application of negative pressure to a wound site and a second tubing from the wound site. The connector assembly includes a valve having a valve body, a pair of proximal lumens connected to one side of the valve body and a pair of distal lumens connected to another side of the valve body opposite the proximal lumens to create first and second valve flow paths across a width of the valve body. An elongate valve shaft is rotatably positioned within the valve body. The valve shaft has a pair of slots along the length of the shaft, one of the slots located along the first valve flow path and the other one of the slots located across the second valve flow path, and a valve handle connected to an exterior portion of the valve shaft for selectively rotating the shaft within the valve body.

The connector assembly also includes an elongate connector having a pair of internal connector flow paths. Each connector flow path terminates at one end of the connector for connecting with the first tubing, and terminates at the other end of the connector for connecting with the proximal lumens of the valve. The slots are configured so that in one rotational orientation of the valve shaft the slots are oriented to open the first and second valve flow paths across the width of the valve body to provide an open position of the valve, and in other rotational orientations of the valve shaft the slots are rotationally located so as to block the first and second flow paths across the width of the valve body and provide a closed position of the valve having positive closure of the valve against flow therethrough.

In another aspect, a connector assembly according to the disclosure includes a valve having a valve body, a proximal lumen connected to one side of the valve body and a distal lumen connected to another side of the valve body opposite the proximal lumen to create a valve flow path across a width of the valve body. An elongate valve shaft is rotatably positioned within the valve body. The valve shaft has a shaft flow passage therethrough, and a valve handle is connected to an exterior portion of the valve shaft for selectively rotating the shaft within the valve body.

The connector assembly also includes an elongate connector having an internal connector flow path terminating at one end of the connector for connecting with the first tubing, and terminating at the other end of the connector for connecting with the proximal lumen of the valve.

The shaft flow path is configured so that in one rotational orientation of the valve shaft the shaft flow path is oriented to open the flow path across the width of the valve body to provide an open position of the valve, and in other rotational orientations of the valve shaft the shaft flow path is rotationally located so as to block the flow path across the width of the valve body and provide a closed position of the valve having positive closure of the valve against flow therethrough.

In a further aspect, a connector assembly according to the disclosure includes a valve having a valve body, a proximal lumen connected to one side of the valve body and a distal lumen connected to another side of the valve body opposite the proximal lumen to create a valve flow path across a width of the valve body. An elongate valve shaft is movably positioned within the valve body, the valve shaft having a shaft flow passage therethrough.

The connector assembly also includes an elongate connector having an internal connector flow path terminating at one end of the connector for connecting with the first tubing, and terminating at the other end of the connector for connecting with the proximal lumen of the valve. The shaft flow path is configured so that in one positional orientation of the valve shaft the shaft flow path is moved to open the flow path across the width of the valve body to provide an open position of the valve, and in other positional orientations of the valve shaft the shaft flow path is moved so as to block the flow path across the width of the valve body and provide a closed position of the valve having positive closure of the valve against flow therethrough.

In another aspect, the disclosure provides a negative pressure wound therapy device that includes a first tubing connectable in flow communication with a source of negative pressure configured for application of negative pressure to a wound site, a second tubing in flow communication with the wound site, and a valve.

The valve includes a valve body in flow communication with the first tubing and the second tubing, and an elongate valve shaft movably positioned within the valve body. The valve shaft has a shaft flow passage therethrough. The shaft flow path is configured so that in one positional orientation of the valve shaft the shaft flow path is moved to open the flow path across the width of the valve body to provide an open position of the valve, and in other positional orientations of the valve shaft the shaft flow path is moved so as to block the flow path across the width of the valve body and provide a closed position of the valve having positive closure of the valve against flow therethrough.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
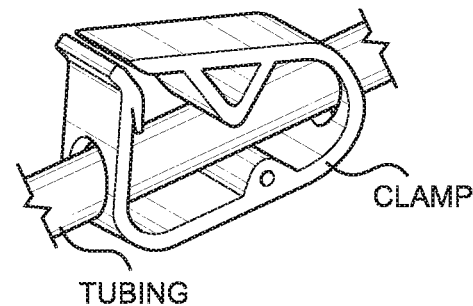
FIG. 1 shows a prior art clamp applied to tubing.

With initial reference to FIGS. 2A-2F there is shown a connector assembly 10 according to the disclosure and configured for a Negative Pressure Wound Therapy (NPWT) application in which the assembly 10 connects to tubing T1 and T2 of a type used in NPWT. The assembly 10 includes a connector 12 and a valve 14. The valve 14 is in an open position in FIGS. 2A-2C and in a closed position in FIGS. 2D-2F.

The assembly 10 is advantageously configured to provide positive closure and to be uncomplicated and easy to use. The assembly 10 has a low profile, compact size and is configured to reduce the risk for injury to a patient or a change in state of the valve 14 if the patient lies on it.

The connector 12 and the valve 14 connect together. The connector 12 connects to the tubing T1 and the valve 14 connects to the tubing T2. The valve 14 is operable to place the tubing T1 and T2 in flow communication when the valve is in an open state and to close off flow communication when the valve is in a closed state.

The tubing T1 and T2 as shown is of a type used in NPWT. While it should be understood that the connector 12 for connecting T1 and T2 may take many forms within the scope of the present disclosure, FIGS. 2A-2F depict one exemplary connector system that is described in detail in U.S. application Ser. No. 16/575,770, filed Sep. 19, 2019, entitled TUBING CONNECTION SYSTEM FOR NEGATIVE PRESSURE WOUND THERAPY, the entire contents of which is incorporated herein by reference.

According to this embodiment, the tubing T1 connects to a NPWT source, such as a suction canister. As shown, the tubing T1 is provided by tubing constructed to have a pair of parallel tubes. The system 10 includes a canister tubing adapter 11 to connect the tubing T1 to the end of the connector 12 opposite the valve 14. The tubing T2 connects to a wound site of a patient and to the valve 14. The tubing T2 may be provided by dual lumen tubing or two parallel tubes. The tubing T1 and T2 each generally have an overall exterior width of about 0.5 inches and an overall exterior thickness of about 0.25 inches.

The canister tubing adapter 11 according to this embodiment is formed of a rigid plastic and includes a first set of projections for connecting the canister connecting end of adapter 11 to the parallel tubes of tubing T1 and a second set of projections for connecting the adapter 11 to the connector 12.

The connector 12 is of molded plastic or elastomeric construction of generally rectangular shape corresponding in profile, e.g., width and thickness dimensions, to the largest dimensions of the second set of projections of adapter 11 and tubing T2 which connects to the valve 14. In preferred embodiments, the connector is formed of a resilient/flexible material such as silicone to slidably engage the second set of projections of the adapter 11, which allows for a significant low profile for the connector 12. For example, the connector 12 has an overall exterior width of about 0.5 inches and an overall exterior thickness of about 0.25 inches, which corresponds to the largest dimensions of the tubing T2.

The connector 12 includes internal flow paths provided by lumens 12a and 12b. The lumens 12a and 12b terminate at one end of the connector 12 for fluidly connecting with the canister tubing adapter 11. The lumens 12a and 12b terminate at the other end of the connector 12 for fluidly connecting with proximal lumens 14a and 14b of the valve 14.

Figure 2A:
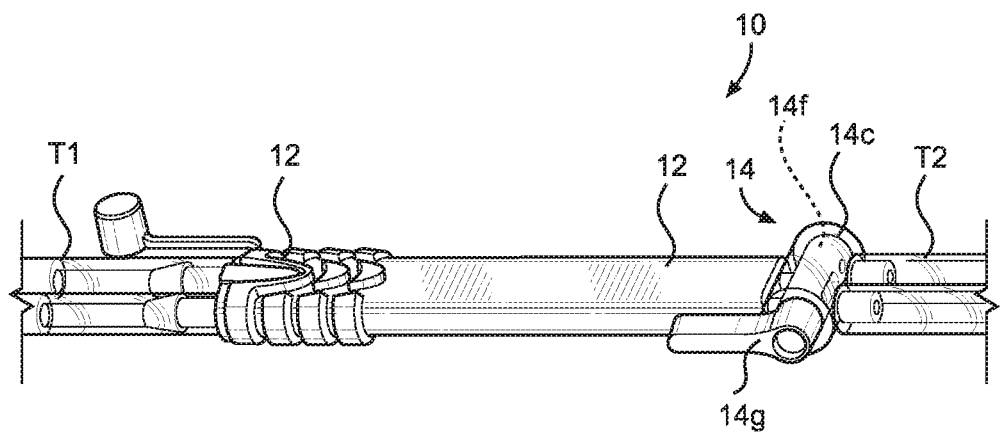
FIGS. 2A-2C show a connector assembly according to the disclosure, with a valve component of the assembly in an open position.
Figure 2B:
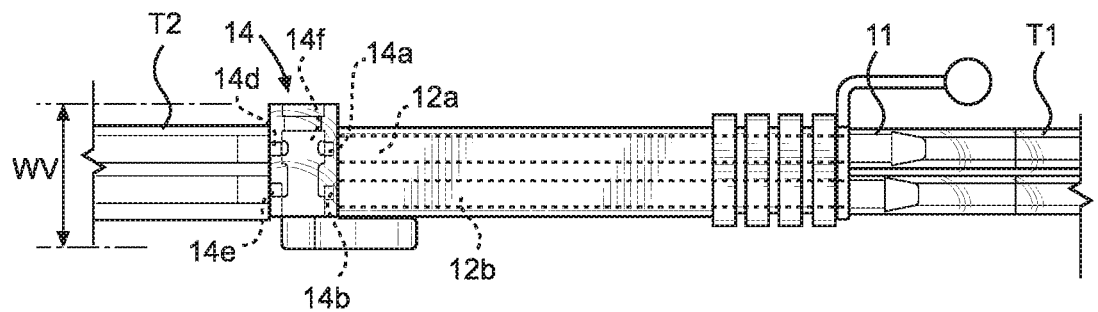
Figure 2C:
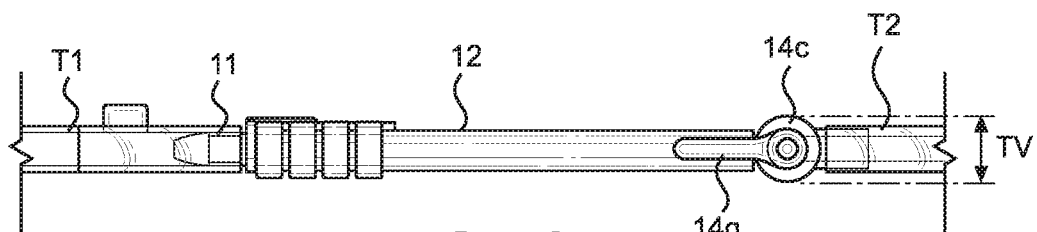
Figure 2D:
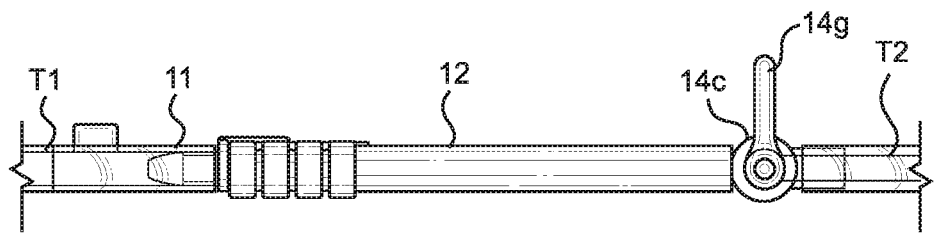
FIGS. 2D-2F show the connector assembly of FIGS. 2A-2C, but with the valve component in a closed position.
Figure 2E:
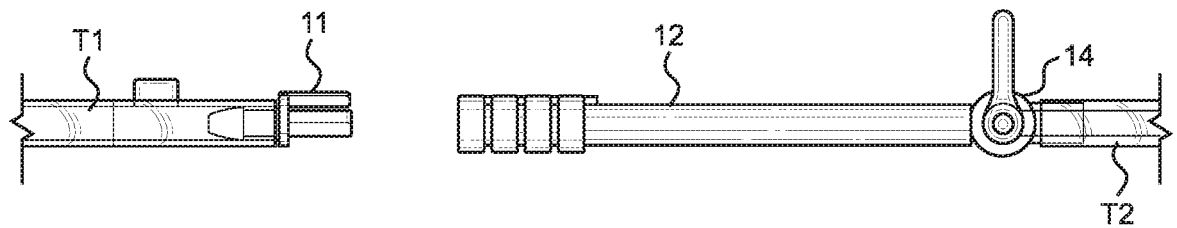
Figure 2F:
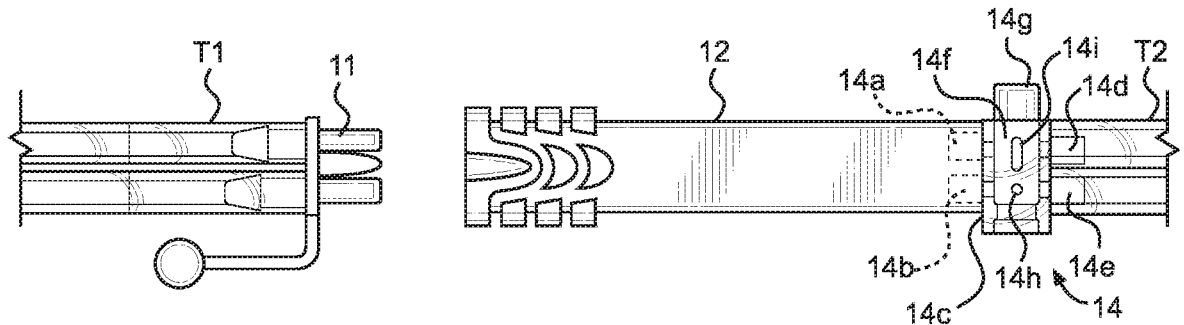
Figures 2G, 2H:
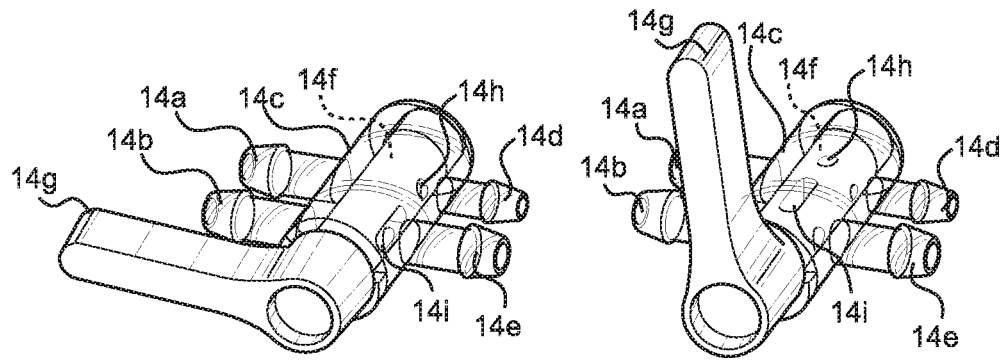
FIGS. 2G and 2H are close-up perspective views of the valve of the connector assembly of FIGS. 2A-2F and FIG. 2I is an exploded perspective view.
Figure 2I:
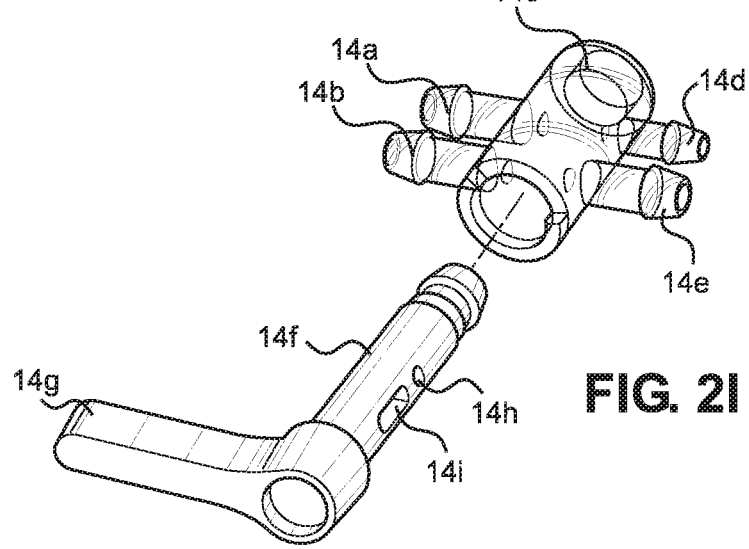

With additional reference to FIGS. 2G, 2H, and 2I, the valve 14 is of molded plastic construction and includes an elongate valve body 14c. The valve body 14c has continuous sidewalls and a hollow interior. The valve body 14c is shown as an open-ended cylinder but may be closed on one end. The proximal lumens 14a and 14b connect to one side of the valve body 14c. Distal lumens 14d and 14e connect at one end to the opposite side of the valve body 14c and are located so that the lumen 14a aligns with the lumen 14d and the lumen 14b aligns with the lumen 14e to create two flow paths across the width of the valve body 14c. The other ends of the distal lumens 14d and 14e fluidly connect to the tubing T2. The valve body 14c is preferably of one-piece molded plastic construction and molded to include the lumens 14a, 14b, 14d and 14e.

A valve shaft 14f is rotatably positioned within the length of the valve body 14c and substantially fills the interior of the valve body 14c. The valve body 14c is preferably clear so that a user can see the orientation of the valve shaft 14f in the valve body 14c. A handle 14g connects to an exterior portion of the shaft 14f for selectively rotating the shaft 14f within the valve body 14c. The valve shaft 14f is preferably of one-piece molded plastic construction and molded to include the handle 14g. A fluid seal may be provided at the juncture of the shaft 14f and the ends of the valve body 14c as by o-rings, gaskets, or other fluid sealing structures.

The shaft 14f includes a pair of spaced apart slots 14h and 14i along its length. The slot 14h is located to align with lumens 14a and 14d and the slot 14i is located to align with the lumens 14b and 14e. The slots 14h and 14i are configured so that in one rotational orientation of the shaft 14f, the slot 14h is oriented to provide a flow path between the lumens 14a and 14d, and the slot 14i is oriented to provide a flow path between the lumens 14b and 14e. However, in other rotational orientations of the shaft 14f, the slots 14h and 14i are rotationally located so as to not provide any flow paths and thus provide positive closure of the valve 14 against flow therethrough.

As shown, the slot 14h is a circular aperture defined through the shaft 14f, and the slot 14i is a rectangular aperture defined through the shaft 14f. The different configurations of the slots 14i and 14h are advantageous to enable the valve 14 to be adaptable for use with different tubing sets T1 and T2. For example, the rectangular slot 14i is useful for circumstances where the two proximal lumens 14a and 14b use the rectangular slot 14i to fluidly connect to a tube with only one lumen (e.g., tubing T2 as shown in FIG. 3C) or where the lumen 14a is not directly aligned with the corresponding lumen of tubing T2 and the flow path is angled slightly. The smaller circular slot 14i is useful for circumstances where the T2 tubing includes one smaller lumen used for pressure sensing and/or sending a secondary pressure to the wound dressing that is to remain isolated from the exudate removal lumen of T1 and T2.

The valve 14 as incorporated into the assembly 10 provides positive closure when closed, as contrasted to the closure mechanism of prior art clamps. The connector assembly 10 is advantageously configured so that it may be easily actuated by a trained or untrained user without requiring excessive levels of force. This is accomplished, for example, by the length of the handle 14g providing a lever to enable ease in rotating the shaft 14f.

Additionally, while the valve 14 is described as having a rotating shaft 14f, it will be understood that the shaft may be movably disposed in the valve body 14c in other ways so as to be movably positionable to provide an open and closed positions. For example, the shaft may be slidingly disposed or have other movement that locates a slot or other flow passage as desired to render the valve open or closed.

The assembly 10 is also configured to visually indicate when the valve 14 is in an open orientation and when it is in a closed orientation. As seen in FIGS. 2A-2C and FIG. 2G, when the valve 14 is open the length or profile of the handle 14g is parallel to and aligned with the length of the connector 12. As seen in FIGS. 2D-2E and FIG. 2H, when the valve 14 is closed, the length or profile of the handle 14g is perpendicular to the length of the connector 12.

The connector assembly 10 is also advantageously configured to have a low profile and compact size and to be configured to reduce the risk for injury to a patient or a change in state of the valve 14 if the patient lies down on it during treatment. In particular, it is desirable that the valve 14 be configured to avoid undesired closure of the valve 14 during wound treatment.

In this regard, it will be understood that the normal or usual state of the connector assembly 10 when used is to have the valve 14 open. The valve 14 is usually only closed temporarily for changing out wound dressings and the like. As noted above, when the valve 14 is open the length or profile of the handle 14g is parallel to and aligned with the length of the connector 12. This orientation of the handle 14g is advantageous to reduce the risk for injury to a patient or a change in state of the valve 14 if the patient lies on it during treatment. With the handle 14g parallel to the connector 12, which is also parallel to the tubing T1 and T2, it would be difficult for the valve 14 to change from the open position by the patient lying on it. Likewise, the location of the handle 14g parallel to the connector 12 also provides a substantially flat profile for the connector assembly 10 which reduces the presence of structure that could cause injury.

In a related aspect, the footprint of the connector assembly 10 is also reduced to provide a small difference in size when the connector assembly 10 is utilized as compared to just the presence of the NWPT tubing without having the connector assembly 10. As noted previously, the connector 12 has an overall exterior width of about 0.5 inches and an overall exterior thickness of about 0.25 inches, which corresponds to the largest dimensions of the tubing T1. The valve 14 is configured so that the presence of the valve 14, when in the open position associated with its state when in use, avoids a bulky increase in the footprint associated with the use of the connector assembly 10.

The connector assembly 10 with the valve 14 in the open position is no more than about 150% of the thickness of the tubing T2. For example, the thickness TV of the valve 14 (FIG. 2C), including the handle 14g, is no more than about 0.5 inches. This avoids the presence of an increased thickness object underneath the patient. In addition, the width of the connector assembly 10 is also desirably reduced. As shown, the width WV of the valve 14 (FIG. 2B) is no more than about 150% of the width of the tubing T2, or 0.75 inches.

Figure 3A:
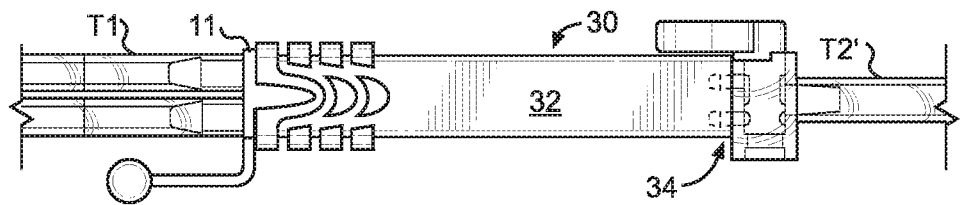
FIGS. 3A-3C show an alternate embodiment of a connector assembly according to the disclosure, with a valve component of the assembly shown in an open position in FIGS. 3A and 3B and in a closed position in FIG. 3C.
Figure 3B:
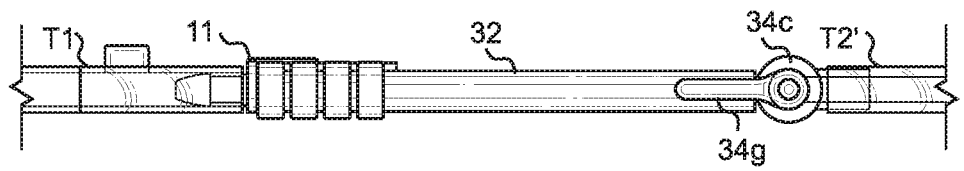
Figure 3C:
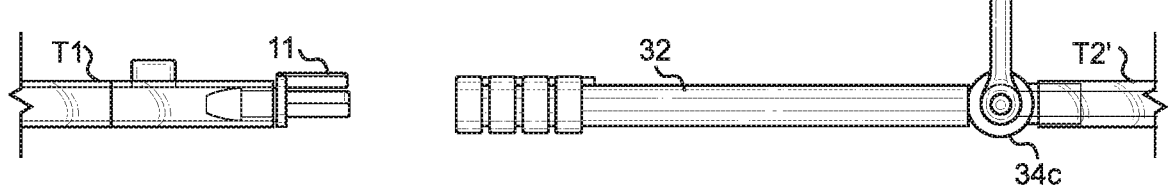
Figures 3D, 3E:
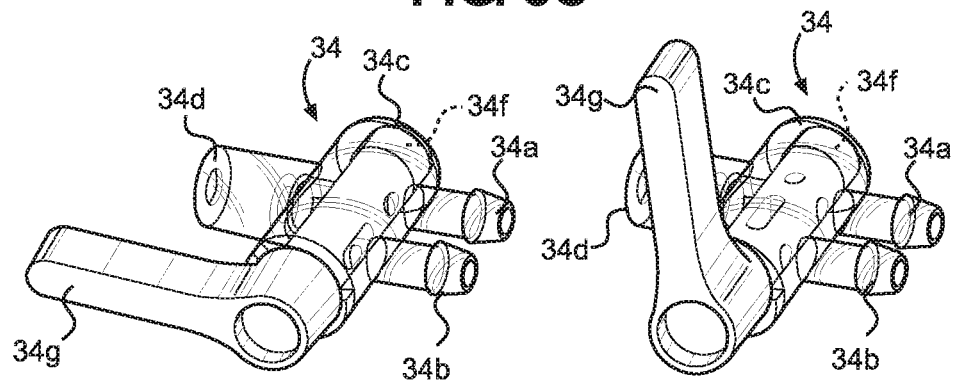
FIGS. 3D and 3E are close-up perspective views of the valve of the connector assembly of FIGS. 3A-3C and FIG. 3F is an exploded perspective view.
Figure 3F:
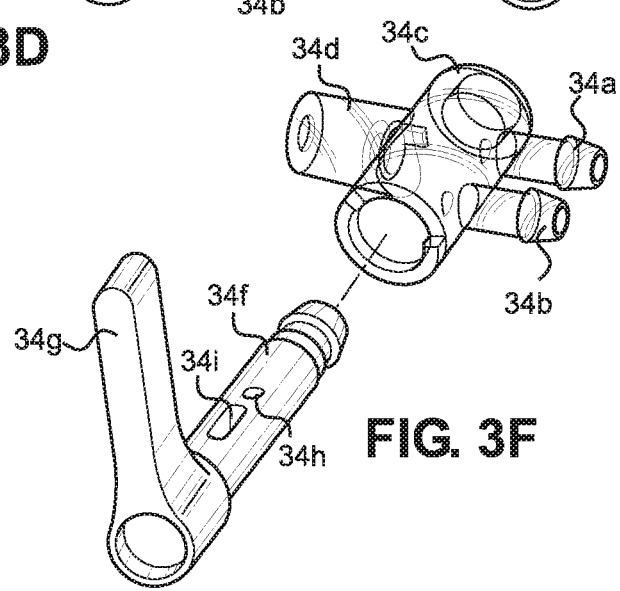

FIGS. 3A-3C depict an alternate embodiment of a connector assembly 30 for negative pressure wound therapy applications. The connector assembly 30 includes a connector 32 and a valve 34. The valve 34 is shown in an open position in FIGS. 3A and 3B and in a closed position in FIG. 3C. The valve is connected to a dual tube assembly on one side and a dual lumen single tube on the other. FIGS. 3D, 3E, and 3F are enlarged views of the valve 34.

The connector assembly 30 connects to the previously described tubing T1 and to tubing T2' of a type used in NPWT. The tubing T2' is similar to the previously described tubing T2, except it is configured as a single tube having multiple lumens.

The connector 32 is substantially similar to the connector 12 and includes internal flow paths that connect at one end to canister tubing adapter 11 and at the other end to the valve 34.

The valve 34 is substantially similar to the valve 14, except it is configured to connect to the tubing T2'. In this regard, the valve includes proximal lumens 34a and 34b on one side of a valve body 34c and a distal lumen 34d on the opposite side of the valve body 34c.

The valve 34 also includes a valve shaft 34f rotatably positioned within the length of the valve body 34c, with a handle 34g connected to an exterior portion of the shaft 34f for selectively rotating the shaft 34f within the valve body 34c. The shaft 34f includes a pair of spaced apart slots 34h and 34i along its length that operate in the manner of the slots 14h and 14i.

Figure 4:
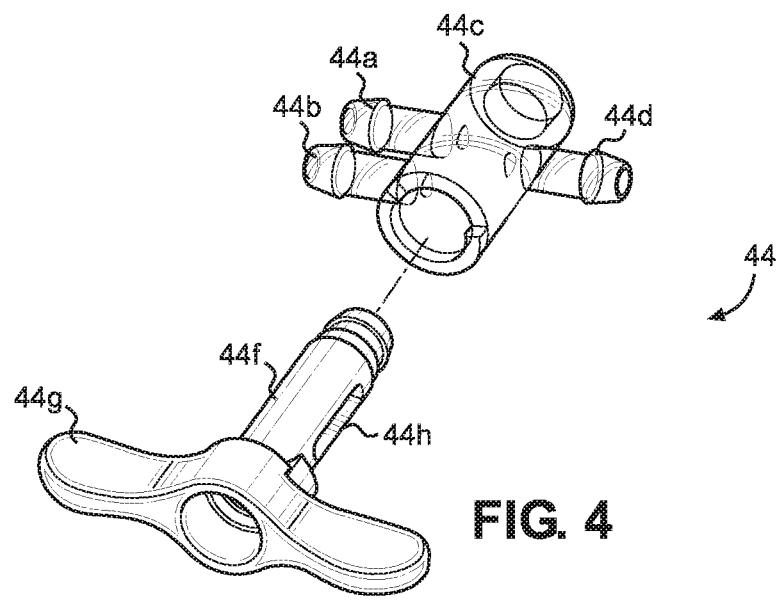
FIG. 4 is an exploded perspective view of an alternate embodiment of a valve.
Figure 5:
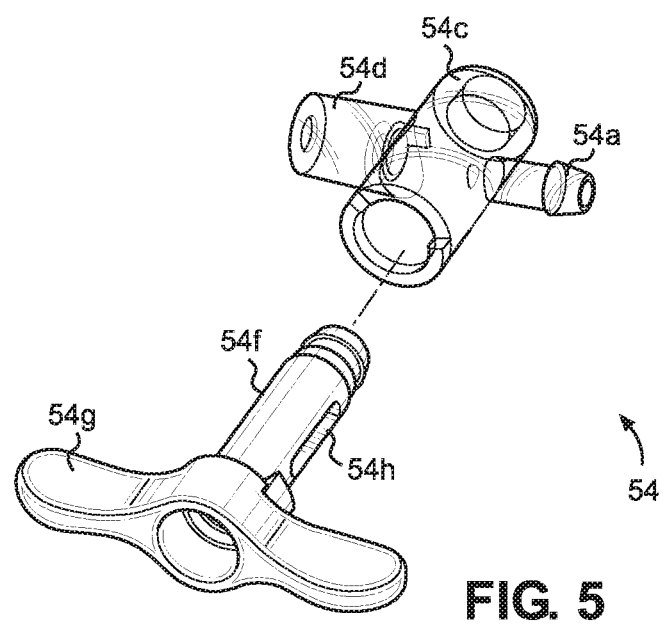
FIG. 5 is an exploded perspective view of another alternate embodiment of a valve.

FIGS. 4 and 5 are views of additional examples of valves 44 and 54 that may be utilized in connection with connector assemblies according to the disclosure. As will be appreciated, the valves 44 and 54 may be connected to a connector in the manner of the connector 12 to connect to tubing for use with NPWT, the connector and the valves differing in configuration based on the tubing they are connecting.

The valve 44 is configured for connection between two single lumen tubes and a single lumen tube. The valve 44 includes proximal lumens 44a and 44b on one side of a valve body 44c and a distal lumen 44d on the opposite side of the valve body 44c.

The valve 44 also includes a valve shaft 44f rotatably positioned within the length of the valve body 44c, with a handle 44g connected to an exterior portion of the shaft 44f for selectively rotating the shaft 44f within the valve body 44c. The shaft 44f includes a single elongate slot 44h along its length that operates in the manner of the slots 14h and 14i.

The valve 54 is configured for connection between a single lumen tube and a single tube having multiple lumens. The valve 54 includes a proximal lumen 54a on one side of a valve body 54c and a distal lumen 54d on the opposite side of the valve body 54c.

The valve 54 also includes a valve shaft 54f rotatably positioned within the length of the valve body 54c, with a handle 54g connected to an exterior portion of the shaft 54f for selectively rotating the shaft 54f within the valve body 54c. The shaft 54f includes a single slot 54h along its length that operates in the manner of the slots 14h and 14i.

Figure 6:
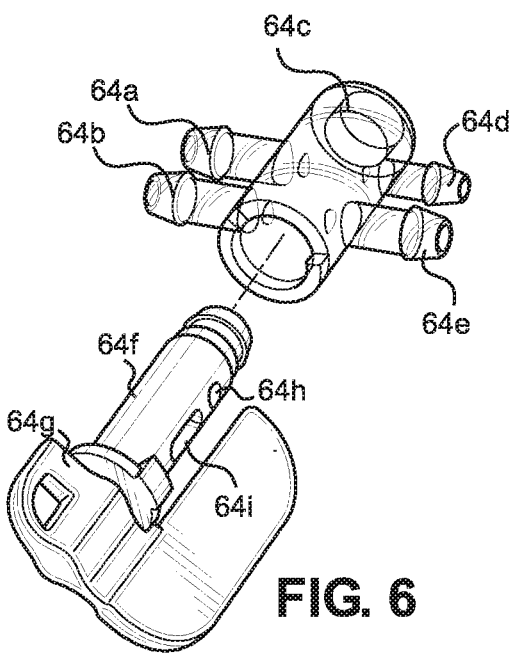
FIG. 6 is an exploded perspective view of another alternate embodiment of a valve and FIG. 6A shows a key component for the valve.
Figure 6A:
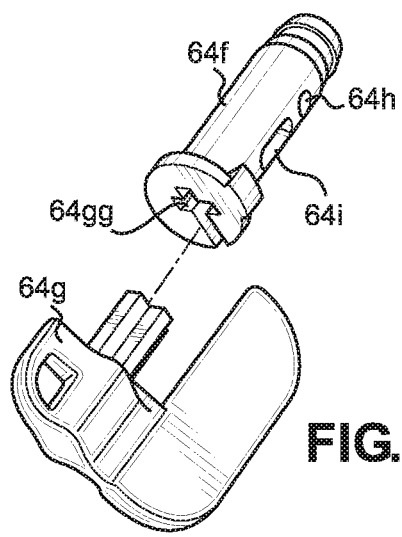

FIGS. 6 and 6A are views of another embodiment of a valve 64 that may be utilized in connection with connector assemblies according to the disclosure and may be connected to a connector in the manner of the connector 12 to connect to tubing for use with NPWT. The valve 64 includes proximal lumens 64a and 64b on one side of a valve body 64c and distal lumens 44d and 44e on the opposite side of the valve body 64c.

The valve 64 also includes a valve shaft 64f rotatably positioned within the length of the valve body 64c, with a removable key 64g that connects to a corresponding receiver 64gg defined on a corresponding outward portion of the shaft 64f. The key 64g may be engaged with the receiver 64gg and is configured in the manner of a handle for selectively rotating the shaft 64f within the valve body 64c. By having the key 64g removable, it will be appreciated that this reduces the profile of the valve 64 and also serves to avoid having any structure located on the valve 64 that could be accidently contacted by the patient to turn off the valve 64. In this regard, it will be appreciated that the key 64g may be carried by a nurse or hung as by a lanyard to the suction equipment nearby, or the like. The shaft 64f includes slots 64h and 64i along its length that operate in the manner of the slots 14h and 14i.

Figure 7:
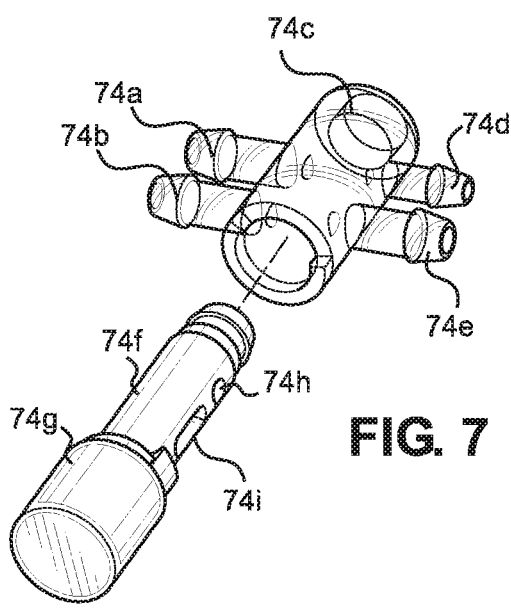
FIG. 7 is an exploded perspective view of yet another alternate embodiment of a valve.

FIG. 7 shows a still further embodiment of a valve 74 that may be utilized in connection with connector assemblies according to the disclosure and may be connected to a connector in the manner of the connector 12 to connect to tubing for use with NPWT. The valve 74 includes proximal lumens 74a and 74b on one side of a valve body 74c and distal lumens 74d and 74e on the opposite side of the valve body 74c.

The valve 74 also includes a valve shaft 74f rotatably positioned within the length of the valve body 54c, with a low-profile knob 74g on an exterior portion of the shaft 74f for selectively rotating the shaft 74f within the valve body 74c. The knob 74g serves as a handle for rotating or otherwise moving the shaft 74f, and the knob 74g may include indicia thereon to indicate open and closed positions of the valve 74. It will be appreciated that the knob 74g reduces the profile of the valve 64 and also serves to avoid having any structure located on the valve 64 that could be accidently contacted by the patient to turn off the valve 64. The shaft 74f includes slots 74h and 74i along its length that operate in the manner of the slots 14h and 14i.

Accordingly, it will be appreciated that the disclosure provides flow controller structures provided by connector assemblies that incorporate a valve and are configured for use with tubing lines of negative pressure wound therapy devices. The connector assemblies are configured so that they may be easily actuated by a user without requiring excessive levels of force, and clearly indicate when in an open orientation and when in a closed orientation. The valve as incorporated into the assembly provides positive closure when closed. The connector assemblies also have a low profile and compact size and are configured to reduce the risk for injury to a patient or a change in state of the valve if the patient lies down on it.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A connector assembly directly connecting between a first tubing having a pair of flow paths from a source of negative pressure configured for application of negative pressure to a wound site and a second tubing having a pair of flow paths from the wound site, the connector assembly comprising:

a valve having (1) a valve body, a pair of proximal lumens connected to one side of the valve body and a pair of distal lumens connected to another side of the valve body opposite the proximal lumens to create first and second valve flow paths across a width of the valve body; and (2) an elongate valve shaft rotatably positioned within the valve body, the valve shaft having a pair of slots spaced apart along the length of the shaft and each extending through a width of the valve shaft, one of the slots located along the first valve flow path and the other one of the slots located across the second valve flow path, and a valve handle connected to an exterior portion of the valve shaft for selectively rotating the shaft within the valve body; and an elongate connector having a pair of internal connector flow paths, each connector flow path terminating at one end of the connector directly connecting with the pair of flow paths of the first tubing, and terminating at the other end of the connector directly connecting with the proximal lumens of the valve, wherein the slots are configured so that in one rotational orientation of the valve shaft the slots are oriented to open the first and second valve flow paths across the width of the valve body to provide an open position of the valve, and in other rotational orientations of the valve shaft the slots are rotationally located so as to block the first and second flow paths across the width of the valve body and provide a closed position of the valve having positive closure of the valve against flow therethrough.

2. The connector assembly of claim 1, wherein the second tubing has an overall exterior thickness, and the connector assembly with the valve in the open position is no more than about 150% of the overall exterior thickness of the second tubing to avoid the presence of an increased thickness object underneath a patient.

3. The connector assembly of claim 1, wherein the second tubing has an overall exterior width, and the valve has a width that is no more than about 150% of the overall exterior width of the second tubing.

4. The connector assembly of claim 1, wherein when the valve is in the open position the valve handle is parallel to the length of the elongate connector.

5. A connector assembly directly connecting between a first tubing from a source of negative pressure configured for application of negative pressure to a wound site and a second tubing from the wound site, the connector assembly comprising:

a valve having (1) a valve body, a proximal lumen connected to one side of the valve body and a distal lumen connected to another side of the valve body opposite the proximal lumen to create a valve flow path across a width of the valve body; and (2) an elongate valve shaft rotatably positioned within the valve body, the valve shaft having a shaft flow passage therethrough, and a valve handle connected to an exterior portion of the valve shaft for selectively rotating the shaft within the valve body; and an elongate connector having an internal connector flow path terminating at one end of the connector directly connecting with the first tubing, and terminating at the other end of the connector directly connecting with the proximal lumen of the valve, wherein the shaft flow path is configured so that in one rotational orientation of the valve shaft the shaft flow path is oriented to open the flow path across the width of the valve body to provide an open position of the valve, and in other rotational orientations of the valve shaft the shaft flow path is rotationally located so as to block the flow path across the width of the valve body and provide a closed position of the valve having positive closure of the valve against flow therethrough.

6. The connector assembly of claim 5, wherein the second tubing has an overall exterior thickness, and the connector assembly with the valve in the open position is no more than about 150% of the overall exterior thickness of the second tubing to avoid the presence of an increased thickness object underneath a patient.

7. The connector assembly of claim 5, wherein the second tubing has an overall exterior width, and the valve has a width that is no more than about 150% of the overall exterior width of the second tubing.

8. The connector assembly of claim 5, wherein when the valve is in the open position the valve handle is parallel to the length of the elongate connector.

9. A connector assembly directly connecting between a first tubing from a source of negative pressure configured for application of negative pressure to a wound site and a second tubing from the wound site, the connector assembly comprising:

a valve having (1) a valve body, a proximal lumen connected to one side of the valve body and a distal lumen connected to another side of the valve body opposite the proximal lumen to create a valve flow path across a width of the valve body; and (2) an elongate valve shaft movably positioned within the valve body, the valve shaft having a shaft flow passage therethrough; and an elongate connector having an internal connector flow path terminating at one end of the connector directly connecting with the first tubing, and terminating at the other end of the connector directly connecting with the proximal lumen of the valve, wherein the shaft flow path is configured so that in one positional orientation of the valve shaft the shaft flow path is moved to open the flow path across the width of the valve body to provide an open position of the valve, and in other positional orientations of the valve shaft the shaft flow path is moved so as to block the flow path across the width of the valve body and provide a closed position of the valve having positive closure of the valve against flow therethrough.

10. The connector assembly of claim 9, wherein the second tubing has an overall exterior thickness, and the connector assembly with the valve in the open position is no more than about 150% of the overall exterior thickness of the second tubing to avoid the presence of an increased thickness object underneath a patient.

11. The connector assembly of claim 9, wherein the second tubing has an overall exterior width, and the valve has a width that is no more than about 150% of the overall exterior width of the second tubing.

12. The connector assembly of claim 9, wherein when the valve includes a valve handle connected to an exterior portion of the valve shaft for selectively rotating the shaft within the valve body to movably position the valve shaft between the open position and the closed position, and when the valve is in the open position the valve handle is parallel to the length of the elongate connector.

13. A negative pressure wound therapy device, comprising:

a first tubing connectable in flow communication with a source of negative pressure configured for application of negative pressure to a wound site;

a second tubing in flow communication with the wound site;

a valve, comprising a valve body in flow communication with the first tubing and the second tubing, and an elongate valve shaft movably positioned within the valve body, the valve shaft having a shaft flow passage therethrough; and an elongate connector having a pair of parallel internal connector flow paths, at least one of the internal connector flow paths terminating at one end of the connector directly connecting with the first tubing, the same internal connector flow path terminating at the other end of the connector directly connecting with the valve the shaft flow path being configured so that in one positional orientation of the valve shaft the shaft flow path is moved to open the flow path across the width of the valve body to provide an open position of the valve, and in other positional orientations of the valve shaft the shaft flow path is moved so as to block the flow path across the width of the valve body and provide a closed position of the valve having positive closure of the valve against flow therethrough; and a valve handle connected to an exterior portion of the valve shaft for selectively rotating the shaft within the valve body to movably position the valve shaft between the open position and the closed position, and when the valve is in the open position the valve handle is parallel to a length axis of the first tubing and a length axis of the second tubing.

14. The negative pressure wound therapy device of claim 13, wherein the second tubing has an overall exterior thickness, and the valve in the open position is no more than about 150% of the overall exterior thickness of the second tubing to avoid the presence of an increased thickness object underneath a patient.

15. The negative pressure wound therapy device of claim 13, wherein the second tubing has an overall exterior width, and the valve has a width that is no more than about 150% of the overall exterior width of the second tubing.

16. A connector assembly directly connecting between a first tubing having a pair of flow paths from a source of negative pressure applying negative pressure to a wound site and a second tubing having a pair of flow paths from the wound site, the connector assembly comprising:

a valve having (1) a valve body, a pair of proximal lumens connected to one side of the valve body and a pair of distal lumens connected to another side of the valve body opposite the proximal lumens to create first and second valve flow paths across a width of the valve body; and (2) an elongate valve shaft rotatably positioned within the valve body, the valve shaft having a pair of slots spaced apart along the length of the shaft and each extending through a width of the valve shaft, one of the slots located along the first valve flow path and the other one of the slots located across the second valve flow path, and a valve handle connected to an exterior portion of the valve shaft for selectively rotating the shaft within the valve body; and an elongated connector positioned between the valve and the first tubing, the elongated connector having a pair of internal flow paths, each connector flow path terminating at one end of the connector and connecting with the pair of flow paths of the first tubing, and terminating at the other end of the connector and connecting with the proximal lumens of the valve, wherein the slots are configured so that in one rotational orientation of the valve shaft the slots are oriented to open the first and second valve flow paths across the width of the valve body to provide an open position of the valve, and in other rotational orientations of the valve shaft the slots are rotationally located so as to block the first and second flow paths across the width of the valve body and provide a closed position of the valve having positive closure of the valve against flow therethrough.

* * * * *